(12) United States Patent
Kimmel

(10) Patent No.: US 9,117,363 B2
(45) Date of Patent: Aug. 25, 2015

(54) INTRAORAL COMMUNICATIONS AND PROCESSING DEVICE

(71) Applicant: Dustin Ryan Kimmel, San Francisco, CA (US)

(72) Inventor: Dustin Ryan Kimmel, San Francisco, CA (US)

( * ) Notice: Subject to any disclaimer, the term of this patent is extended or adjusted under 35 U.S.C. 154(b) by 274 days.

(21) Appl. No.: 13/831,940

(22) Filed: Mar. 15, 2013

(65) Prior Publication Data

US 2013/0278396 A1  Oct. 24, 2013

Related U.S. Application Data

(60) Provisional application No. 61/612,398, filed on Mar. 19, 2012.

(51) Int. Cl.
*A61B 5/103* (2006.01)
*A61F 4/00* (2006.01)
*G08C 17/02* (2006.01)

(52) U.S. Cl.
CPC . *G08C 17/02* (2013.01); *A61F 4/00* (2013.01); *G08C 2201/112* (2013.01); *G08C 2201/32* (2013.01)

(58) Field of Classification Search
None
See application file for complete search history.

(56) References Cited

U.S. PATENT DOCUMENTS

| | | | |
|---|---|---|---|
| 4,605,927 A * | 8/1986 | Katz et al. | 340/4.14 |
| 4,983,786 A * | 1/1991 | Stevens et al. | 178/18.01 |
| 5,212,476 A * | 5/1993 | Maloney | 340/4.11 |
| 5,460,186 A | 10/1995 | Buchhold | |
| 5,523,745 A | 6/1996 | Fortune et al. | |
| 5,579,284 A | 11/1996 | May | |
| 5,603,065 A | 2/1997 | Baneth | |
| 5,631,669 A | 5/1997 | Stobbs et al. | |
| 5,792,067 A | 8/1998 | Karell | |
| 5,828,758 A | 10/1998 | Byce et al. | |
| 6,222,524 B1 | 4/2001 | Salem et al. | |
| 6,400,353 B1 | 6/2002 | Ikehara et al. | |
| 6,419,649 B1 * | 7/2002 | Klein | 601/70 |
| 7,071,844 B1 | 7/2006 | Moise | |
| 7,918,808 B2 * | 4/2011 | Simmons | 600/590 |

(Continued)

OTHER PUBLICATIONS

Nutt, Wolfgang et. al., Tongue-mouse for quadriplegics, J. Micromech. Microeng. 8, Aug. 12, 1997, p. 155-p. 157, IOP Publishing Ltd, UK.

*Primary Examiner* — Ariel Balaoing
*Assistant Examiner* — John Bamert

(57) ABSTRACT

Methods, apparatuses, systems, and computer-readable media for communicating via an electronic device for use in a mouth environment of an animal and resistant to damage from bodily fluids and pressure. The device can be pierced through a tongue, a lip, or a cheek, anchored to a tooth or a teeth of the mandible, or implanted in (or attached to an implant in) the maxilla or mandible. The device includes: a power device, which can power the apparatus, a memory storage device, which can store and recall data; a communications subsystem, which communicates with one or more remote devices; an output device, which creates stimulus directly or indirectly observable in the mouth environment; an input device, which can create signals according to activity in the mouth environment and can send them to the memory storage device and/or processor; and a processor coupled to the memory storage device, the communication subsystem, the output device and the input device.

22 Claims, 9 Drawing Sheets

(56) References Cited

U.S. PATENT DOCUMENTS

| | | |
|---|---|---|
| 2003/0120183 A1* | 6/2003 | Simmons ................... 600/595 |
| 2005/0240253 A1* | 10/2005 | Tyler et al. ................. 607/134 |
| 2007/0106138 A1* | 5/2007 | Beiski et al. ............... 600/349 |
| 2009/0051564 A1* | 2/2009 | Najanguaq Sovso Andreasen Strujik ................. 340/825.19 |
| 2009/0306741 A1* | 12/2009 | Hogle et al. ................ 607/54 |
| 2011/0141052 A1* | 6/2011 | Bernstein et al. ........... 345/174 |
| 2012/0259554 A1* | 10/2012 | Chen et al. ................. 702/19 |

\* cited by examiner

Generating stimulus to a tongue of a user
to communicate a user interface to the user

810

Detecting an analog input
from an environment of the tongue of the user

820

Interpreting the analog input from the environment
as one or more user commands

830

INTRAORAL COMMUNICATIONS AND PROCESSING DEVICE

CROSS-REFERENCE TO RELATED APPLICATIONS

This patent application claims the benefit of U.S. Provisional Patent Application Ser. No. 61/612,398 filed Mar. 19, 2012, and entitled "Intraoral Processing and Communications Device," which is incorporated by reference herein in its entirety for all purposes.

BACKGROUND

Aspects of the disclosure relate to computing technologies. In particular, aspects of the disclosure relate to mobile computing device technologies, such as systems, methods, apparatuses, and computer-readable media of oral or intraoral computing and communications technology.

In anatomy, the area known as "the mouth" is a nexus of biological processes, and can be capable of great sensation, dexterity, and communication—abilities that could be used for fine control, interaction, and exchange of information. However, its harsh, dynamic and vulnerable environment makes presenting a user interface to, and maintaining direct, prolonged access to the abilities and perspective of the mouth a difficulty.

Mouth-activated communications devices and orally-disposed controllers can be connected to and used to control such devices as wheelchairs, computers, and text-to-speech devices, and the like. This communication typically happens through a wired connection. These mouth-activated communications devices are limiting in their ability to connect without cumbersome wires. These mouth-activated communications devices are also limiting in their ability to be integrated with and used as part of an everyday life and/or lifestyle, as they block and/or hinder normal body functions and operation such as eating, talking, breathing, etc. These devices are also limiting in that they engage and/or occupy the user's tongue outside the range of its normal activities in actions for input. Mouth-activated communications devices are also limiting in that they are not based on the tongue, so they can't make use of the tongue-centric perspective, data, and/or capabilities (like the ability to track motions of the tongue from the perspective of the tongue (such as orientation during speech) and the input that can be gathered from this perspective, the shape-changing abilities of the tongue around a piercing, the range of sensory and control capabilities of the full tongue (as opposed to just the tip of the tongue) the dexterity of the tongue (such as rotation, curling, etc.), and/or the ability of the tongue to be split into two independently mobile halves), can't be combined in multiple instances on the tongue and/or other areas of the mouth.

Orally-disposed communications devices and mouth-activated controllers can often be linked to other devices, however their functionality is usually limited to sending data to these other devices for control or logging purposes, wherein no feedback or dynamic oral user interface is communicated to or communicates with the wearer. These orally-disposed communications devices and mouth-activated controllers are limiting in their lack of delivery of feedback of a user interface or information about the controlled device to the user. Accordingly, further advances in intraoral processing and communications devices have been needed.

Embodiments of the invention help solve these and other problems.

SUMMARY

The invention is a mobile processing and communications device, that can be wielded directly from the mouth. A user, wielding the device from the mouth, can observe the device's dynamic oral user interface, and, using this interface, can control the device and/or wirelessly communicate with other devices.

An embodiment of the present disclosure relates to an electronic device having an apparatus which includes a housing for use in a mouth environment of an animal and resistant to damage from bodily fluids and pressure. The housing can be pierced through a tongue, a lip, or a cheek, anchored to a tooth or a teeth of the mandible, or implanted in (or attached to an implant in) the maxilla or mandible. The housing includes: a power device, which can power the apparatus, a memory storage device, which can store and recall data; a communications subsystem, which communicates with one or more remote devices; an output device, which creates stimulus directly or indirectly observable in the mouth environment; an input device, which can create signals according to activity in the mouth environment and can send them to the memory storage device and/or processor; and a processor coupled to the memory storage device, the communication subsystem, the output device and the input device. An advantage of the present invention is that it is more effective in harnessing the communicative power of the tongue than current inventions.

The housing can be one or more of a piercing jewelry, a piercing stud, a mandible retainer, a mandible bridge, a dental implant and an attachable to a dental implant. The piercing jewelry can be a barbell shape. The piercing jewelry housing is advantageous because it allows the user to wield the device from and/or with the tongue; this allows the device greater contact with the dexterity and perceptive power of the tongue, as well as locating it within a nexus of life processes. The mandible retainer and/or bridge is advantageous because it allows the user to wield the device from the lower jaw with the tongue in a relaxed, forward position (instead of reaching up into the maxilla). The dental implant housing is advantageous as it can be put in place for many years, perhaps permanently, and (if replacing a tooth) takes up no extra room in the mouth environment. The dental implant housing is also advantageous because it allows stimulation of deeper gum tissue.

The electronic device further includes a power device deriving power from one or more of energy of an internal battery, wireless energy transfer, energy from chemical or electrical reactions with the surrounding mouth environment, energy from chemical reactions with the blood of the user, energy from the physical flow of the bloodstream of the user, and kinetic energy of the motion of the animal.

The electronic device can further include a communications device that can be one or more of an EMF transmitter/receiver device, a Radio Frequency Identification (RFID) tag, a Bluetooth device, a WiFi device, and a cellular device.

The electronic device can further include an output device that can be one or more of a mechanical wave generator device, an electrical stimulator device, a vibration device, and a physical release device.

The electronic device can further include an input device that can be one or more of a touch sensor device, a material sensor device, a pressure sensor device, a movement tracking sensor device, an orientation sensor device, an acceleration sensor device, a temperature sensor device, an air sensor device, and a light sensor device.

The electronic device can further include a memory storage device that can include one or more application programs.

Another embodiment of the present disclosure relates to an electronic device having an apparatus including a housing inside the mouth of an animal and resistant to damage from bodily fluids and pressure. The housing can be one of a tongue piercing, a lip piercing, and a cheek piercing. The housing can further include: a power device for powering the apparatus; a processor communicatively coupled to an output device, input device, memory storage device, and communications subsystem. The output device can generate one or more stimulii in the mouth environment. The input device can create signals associated with the analog input in the mouth. The memory storage device can be communicatively coupled to the processor for storing and recalling data. The communications subsystem can communicate with one or more remote devices. The housing can include a piercing jewelry of barbell shape. The barbell shape is advantageous because it allows the housing to stay in the tongue but still to rotate in its piercing site.

The electronic device can further includes a power device which can derive power from the energy of an internal battery.

The electronic device can further include a communications device which can include an EMF transmitter/receiver device.

The electronic device can further include an output device includes one or more of a mechanical wave generator device, an electrical stimulator device, a vibration device, and a physical release device.

The electronic device can further include an input device which can include one or more of a touch sensor device, a pressure sensor device, a movement tracking sensor device, an orientation sensor device, an acceleration sensor device, a temperature sensor device, an air sensor device, and a light sensor device.

The electronic device can further include a memory storage device that can include one or more application programs.

An exemplary method for communicating includes generating a stimulus to a tongue of a user to communicate a user interface to the user; detecting an analog input from an environment of the tongue of the user; and interpreting the analog input from the environment as one or more user commands.

In certain embodiments the stimulus can be generated using a tongue-pierced device.

In certain embodiments the stimulus can be generated using a device anchored to a tooth or a teeth of the mandible.

In certain embodiments the stimulus can be generated using a device implanted in (or attached to an implant in) the maxilla or mandible.

In certain embodiments the stimulus can be generated by one or more of creating vibration, causing electric shocks from electrodes, and dispensing matter.

In certain embodiments the analog input can be detected from one or or more of sensing touch, orientation, acceleration, pressure, and sound at the environment of the tongue.

In an example non-transitory computer readable storage medium, wherein the non-transitory computer readable storage medium comprises instructions executable by a processor, the instructions comprising instructions to generate a stimulus to a tongue of a user to communicate a user interface to the user; detect an analog input from an environment of the tongue of the user, and interpret the analog input from the environment as one or more user commands.

In one implementation of the non-transitory computer readable storage medium the stimulus can be generated using a tongue-pierced device.

In another implementation of the non-transitory computer readable storage medium the stimulus can be generated using a device anchored to a tooth or a teeth of the mandible.

In another implementation of the non-transitory computer readable storage medium the stimulus can be generated using a device implanted in (or attached to an implant in) the maxilla or mandible.

In another implementation of the non-transitory computer readable storage medium the stimulus can be generated by one or more of creating vibration, causing electric shocks from electrodes, and dispensing matter.

In another implementation of the non-transitory computer readable storage medium the analog input can be detected from one or more of sensing touch, orientation, acceleration, pressure, and sound at the environment of the tongue.

An example device or apparatus for communicating includes means for generating a stimulus to a tongue of a user to communicate a user interface to the user, means for detecting an analog input from an environment of the tongue of the user, and means for interpreting the analog input from the environment as one or more user commands.

In certain embodiments the device or apparatus can include means for generating the stimulus using a tongue-pierced device.

In certain embodiments the device or apparatus can include means for generating the stimulus using a device anchored to a tooth or a teeth of the mandible.

In certain embodiments the device or apparatus can include means for generating the stimulus using a device implanted in (or attached to an implant in) the maxilla or mandible.

In certain embodiments the device or apparatus can include means for generating the stimulus by causing vibration, causing electric shocks from electrodes, and dispensing matter.

In certain embodiments the device or apparatus can include means for detecting the analog input from one or or more of sensing touch, orientation, acceleration, pressure, and sound at the environment of the tongue.

The foregoing has outlined rather broadly the features and technical advantages of examples according to the disclosure in order for the detailed description that follows to be better understood. Additional features and advantages will be described hereinafter. The conception and specific examples disclosed can be readily utilized as a basis for modifying or designing other structures for carrying out the same purposes of the present disclosure. Such equivalent constructions do not depart from the spirit and scope of the appended claims. Features which are believed to be characteristic of the concepts disclosed herein, both as to their organization and method of operation, together with associated advantages, will be better understood from the following description when considered in connection with the accompanying figures. Each of the figures is provided for the purpose of illustration and description only and not as a definition of the limits of the claims.

BRIEF DESCRIPTION OF THE DRAWINGS

The following description is provided with reference to the drawings, where like reference numerals are used to refer to like elements throughout. While various details of one or more techniques are described herein, other techniques are also possible. In some instances, well-known structures and devices are shown in block diagram form in order to facilitate describing various techniques.

A further understanding of the nature and advantages of examples provided by the disclosure can be realized by reference to the remaining portions of the specification and the drawings, wherein like reference numerals are used throughout the several drawings to refer to similar components. In some instances, a sub-label may be associated with a reference numeral to denote one of multiple similar components.

FIG. 8 is a flow diagram of the general method of communicating used by some embodiments of the invention.

DETAILED DESCRIPTION

Figure 1:
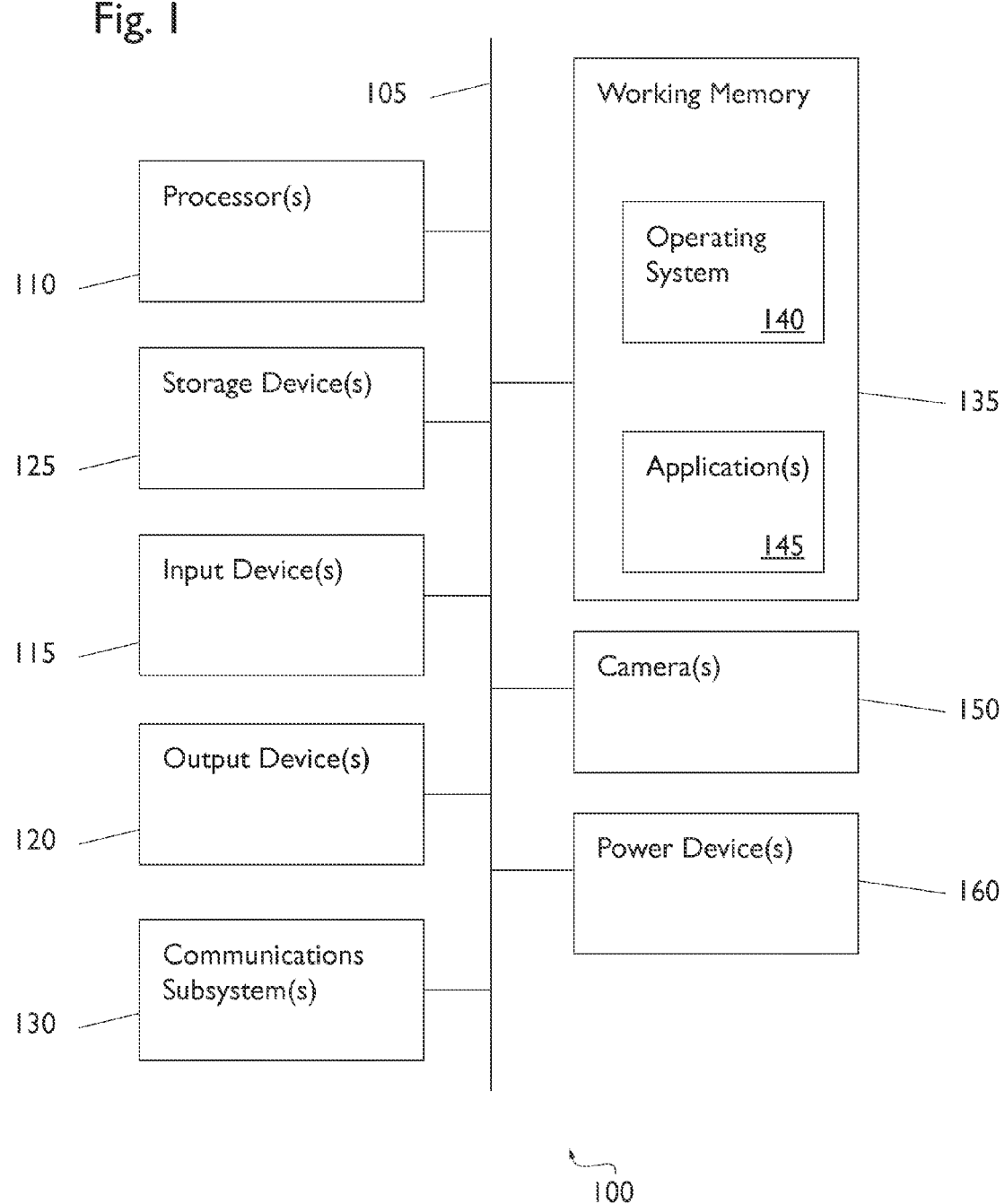
FIG. 1 illustrates an exemplary device in which one or more aspects of the disclosure may be implemented.

Embodiments of the present disclosure are described herein with reference to the drawing figures.

FIG. 1 illustrates an exemplary device incorporating parts of the device employed in practicing embodiments of the invention. An exemplary device as illustrated in FIG. 1 may be incorporated as part of the described computerized device below. For example, device 100 can represent some of the components of a mobile device. A mobile device may be any computing device with an input sensory unit, like a touchpad, and an output unit, like a speaker. Examples of a mobile device include, but are not limited to, video game consoles, tablets, smart phones, camera devices and any other portable devices suitable for performing embodiments of the invention. FIG. 1 provides a schematic illustration of one embodiment of a device 100 that can perform the methods provided by various other embodiments, as described herein, and/or can function as the host device, a remote kiosk/terminal, a point-of-sale device, a mobile device, a set-top box and/or a device. FIG. 1 is meant only to provide a generalized illustration of various components, any or all of which may be utilized as appropriate. FIG. 1, therefore, broadly illustrates how individual system elements may be implemented in a relatively separated or relatively more integrated manner. FIG. 1 is an exemplary portable processing device or mobile device that may use components as described in reference to FIG. 1. In some embodiments, only some of the components described in FIG. 1 are implemented and enabled to perform embodiments of the invention. For example, a touchpad device may have one or more touchpads, storage, or processing components along with other components described in FIG. 1.

The device 100 is shown comprising hardware elements that can be electrically coupled via a bus 105 (or may otherwise be in communication, as appropriate). The hardware elements may include, but are not limited to, one or more power devices 160, including without limitation one or more power storage and/or distribution devices (such as a battery) and/or one or more power generation, storage, and distribution devices (such as a combination of power generator, power management device, and a battery). In other embodiments, power and/or data might be distributed via one or more separate buses, or a combination of buses, and/or individual components of device 100 might have independent or external power device(s) 160. The hardware elements may include, but are not limited to, one or more processors 110, including without limitation one or more general-purpose processors and/or one or more special-purpose processors (such as digital signal processing chips, graphics acceleration processors, random number generator and logic for cryptography, and/or the like). The hardware elements may also include one or more signal-creating input devices 115 which can sense analog input. One or more input devices 115 can include without limitation a touchpad, sensors, sensor devices (exemplary sensor devices discussed in figures and later paragraphs), a microphone, a pushbutton, a gyroscope, and/or an accelerometer and/or the like. For example, a microphone might sense the analog input of sound. The hardware elements may also include one or more output devices 120, which can produce a stimulus to a subject and/or environment and can include without limitation a vibration device, a light device, an electric-shock and/or electrode-array device, devices (exemplary devices discussed in figures and later paragraphs), and/or the like. For example, an electrode-array device might produce a stimulus of an electric shock to a person it might be touching. In addition, hardware elements may also include without limitation one or more cameras 150, as shown in FIG. 1, for acquiring image content.

In other embodiments one or more input devices 115 can include, without limitation: movement tracking sensor devices such as an LED/photo-diode tracking device (as found in an optical mouse) and/or more advanced visual-tracking devices, which can be used to observe and report movement information; pressure sensor devices (like a microphone device, piezoelectric devices, and/or an air pressure sensor device), which can be used to observe and report pressure change information such as sound, vocalizations, breathing or physical stress changes; temperature sensor devices (like a thermometer device), which can be used to observe and report body heat, respiration temperature, external temperature, general temperature, or other temperature information; touch sensor devices (like button devices, switch devices, slider devices, bite pressure devices, piezoelectric devices optical touch devices, rotation sensor devices, optical movement tracking devices and touchpad devices), which can be used to observe and report direct physical interaction and movement information and even indirect physical interaction and movement information; air sensor devices (like machine olfaction devices, gas flow monitor devices, and/or chemical identification devices), which can be used to observe and report breathing, temperature, humidity, pressure, gas flow, gas state, and air quality information; material sensor devices (like machine taste devices, chemical sensor devices, salinity sensor devices, blood analysis devices and/or pH sensor devices), which can be used to observe and report chemical makeup information or other physical characteristics of breath, food, saliva, bodily fluids and/or organs; light sensor devices (like photodiode devices, infrared light sensor devices, light meter devices and/or camera devices), which can be used to observe and report light, distance, thickness, color and movement information; acceleration sensor devices (like an accelerometer or a pedometer device) which can be used to observe and report velocity and/or acceleration change and movement force information; and orientation sensor devices (like a compass device, or a digital gyroscope device), which can be used to observe and report orientation and movement information.

In other embodiments one or more stimulus and/or output devices 120 can include, without limitation: electrical stimulator devices (like electrode devices, electrode-array devices, and/or shock devices), which can be used to communicate to or stimulate the user and/or others by applying electric current via electrodes to the surrounding environment (such as to the surface of the tongue, to the interior of the mouth, or to and/or into the tissue of an embedding site); light devices (like indicator light devices, infrared light devices, or laser light or laser pointer devices), which can be used to communicate to the user or others and/or illuminate by creating visible, infrared and/or ultraviolet light and/or light beams (and projected beams can be used as pointing devices or projector displays by the user); tactile, actuator, or touch-based vibration devices (like vibration motor devices, and Braille terminal devices), which can be used to communicate to the user or others by creating vibration based feedback and tactile or touchable states; physical release devices (like metered chemical release devices (which could release chemicals), spray devices, dispenser devices, or pill dispenser devices), which can be used to release matter to communicate to and/or or stimulate the user and others by releasing or dispensing matter into the surrounding environment; and mechanical wave generator devices (like speaker devices and/or vibration devices and/or bone-conduction transducer devices), which can be used to communicate to the user and others by creating sound and other mechanical waves.

In other embodiments one or more power devices 160 could reside apart from the rest of device 100, including, without limitation, outside any primary enclosure, in a separate enclosure, and/or connected by a tether and/or power transfer device. In other embodiments power may be generated by one or more power devices 160 from, including, without limitation, interaction with the chemicals in the internal and/or external environment (such as electrical interaction as in a battery, by using an exposed anode and cathode), and/or interaction with the chemicals and/or pressure of the bloodstream of the user, and/or interaction with the external environment and/or functioning of organisms and/or one or more devices hosted within the device (such as with a genetically-engineered biofuel device and/or biofuel organism that generates power from oxygen and glucose in the bloodstream of a wearer), and/or interaction with temperature differences in the external environment (such as by coupling a generator with a Stirling engine or other heat engine), and/or by movement (such as by coupling a generator with a self-winding mechanism of the type as used in a self-winding watch and/or capturing the energy of actions performed on device 100), and/or by wireless energy transfer (such as by direct induction, resonant magnetic induction or electromagnetic power reception devices (such as RFID tags)).

The device 100 may further include without limitation (and/or be in communication with) one or more non-transitory storage devices 125, which can comprise, without limitation, local and/or network accessible storage, and/or can include, without limitation, a hard drive, a drive array, an optical storage device, a solid-state storage device such as a random access memory ("RAM") and/or a read-only memory ("ROM"), which can be programmable, flash-updateable and/or the like. Such storage devices may be configured to implement any appropriate data storage, including, without limitation, various file systems, database structures, and/or the like.

The device 100 might also include without limitation one or more communications subsystems 130, which can include without limitation a network communications device (wireless and/or wired), an infrared communication device, an optical communications device, a wireless communication device and/or chipset (such as a Bluetooth® device, an RFID device (active, passive, or battery-assisted passive), an 802.11 device, a WiFi device, a WiMax device, cellular communication facilities), any kind of signaling circuitry or communications device, including any kind of EMF transmitter/receiver device (which may, without limitation, transmit, receive, both transmit and receive, reflect and/or alter an outside transmission, and the like) a wireless communications device, and/or the like. Bluetooth is a proprietary open wireless technology standard for wirelessly exchanging data, and RFID, Radio-frequency identification, is a wireless non-contact technology that uses radio-frequency electromagnetic fields to transfer data. Communications subsystem 130 could include, without limitation, one or more antenna devices to broadcast and receive electromagnetic signals. Communications subsystem 130 may permit data to be exchanged with an external and/or remote device (such as a mobile device) and/or network, other devices, and/or any other devices described herein. As described herein, the term "external device" and "remote device" may be used interchangeably, without limiting the scope of the disclosure. For example, the external device discussed above may be the same device as the remote device 930 discussed in FIG. 9.

In many embodiments, the device 100 will further comprise a non-transitory working memory 135, which can include a RAM or ROM device, as described above.

Other devices that communications subsystem 130 may permit data to be exchanged with include without limitation other and/or similar embodiments of the invention in and/or on and/or throughout the body of the wearer, and/or in and/or on and/or the body or bodies of one or more other wearers of such devices.

The device 100 also can comprise software elements, shown as being currently located within the working memory 135, including an operating system 140, device drivers, executable libraries, and/or other code, such as one or more programs or application(s) 145, which may comprise computer programs provided by various embodiments, and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be stored on a computer-readable storage medium, such as the storage device(s) 125 described above. In some cases, the storage medium might be incorporated within a device, such as device 100. In other embodiments, the storage medium might be separate from a device (e.g., a removable medium, such as a compact disc), and/or provided in an installation package, such that the storage medium can be used to program, configure and/or adapt a general purpose computer with the instructions/code stored thereon. These instructions might take the form of executable code, which can be executable by the device 100 and/or might take the form of source and/or installable code, which, upon compilation and/or installation on the device 100 (e.g., using any of a variety of generally available compilers, installation programs, compression/decompression utilities, etc.), then takes the form of executable code.

Substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

Some embodiments may employ a device (such as the device 100) to perform methods in accordance with the disclosure. For example, some or all of the procedures of the described methods may be performed by the device 100 in response to processor 110 executing one or more sequences of one or more instructions (which might be incorporated into the operating system 140 and/or other code, such as an application 145) contained in the working memory 135. Such instructions may be read into the working memory 135 from another computer-readable medium, such as one or more of the storage device(s) 125. Merely by way of example, execution of the sequences of instructions contained in the working memory 135 might cause the processor(s) 110 to perform one or more procedures of the methods described herein.

The terms "machine-readable medium" and "computer-readable medium," as used herein, may refer to any article of manufacture or medium that participates in providing data that causes a machine to operate in a specific fashion. In an embodiment implemented using the device 100, various computer-readable media might be involved in providing instructions/code to processor(s) 110 for execution and/or might be used to store and/or carry such instructions/code (e.g., as signals). In many implementations, a computer-readable medium is a physical and/or tangible storage medium and/or memory storage device. Such a medium may take many forms, including, but not limited to, non-volatile media, volatile media, and transmission media. Non-volatile media may include without limitation optical and/or magnetic and/or solid state drives, such as the storage device(s) 125. Volatile media include, without limitation, dynamic memory, such as the working memory 135. "Computer readable medium," "storage medium," and other terms used herein do not refer to transitory propagating signals. Common forms of physical and/or tangible computer-readable media include, for example, a floppy disk, a flexible disk, hard disk, magnetic tape, a solid state memory device, or any other magnetic medium, a CD-ROM, any other optical medium, punchcards, papertape, any other physical medium with patterns of holes, a RAM, a PROM, an EPROM, a FLASH-EPROM, or any other memory chip or cartridge.

Various forms of computer-readable media may be involved in carrying one or more sequences of one or more instructions to the processor(s) 110 for execution. Merely by way of example, the instructions may initially be carried on a magnetic disk and/or a solid state memory device and/or optical disc of a remote computer.

The communications subsystem 130 (and/or components thereof) generally will receive the signals, and the bus 105 then might carry the signals (and/or the data, instructions, etc. carried by the signals) to the working memory 135, from which the processor(s) 110 retrieves and executes the instructions. The instructions received by the working memory 135 may optionally be stored on a non-transitory storage device 125 either before or after execution by the processor(s) 110.

Figure 2:
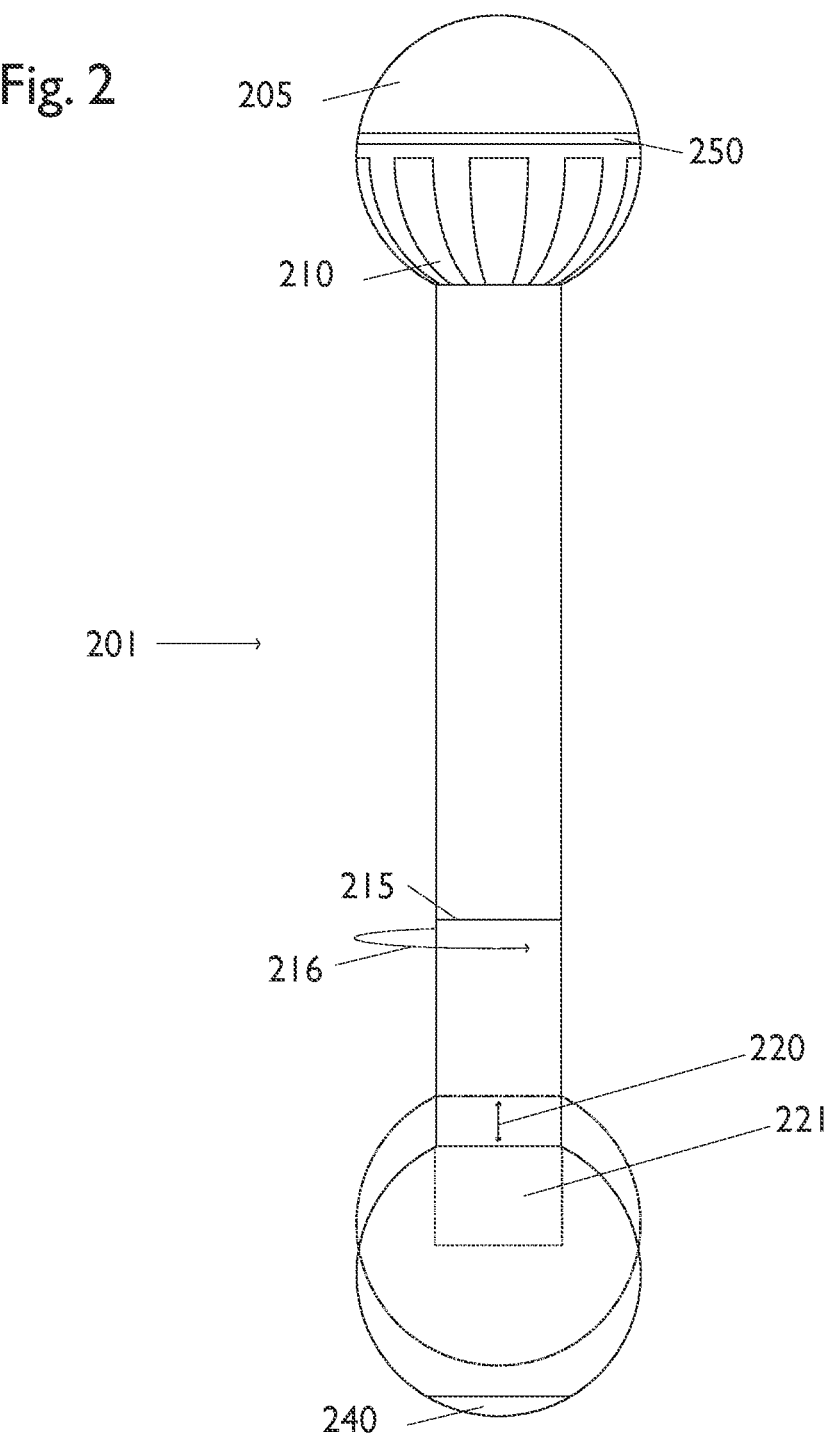
FIG. 2 illustrates a perspective view of an embodiment of the device, a barbell-shaped stud that can be worn embedded in or pierced through mouth tissue.

FIG. 2 illustrates an embodiment of the invention as a perspective view of a barbell-shaped jewelry or stud. The stud can include without limitation barbell-shaped enclosure 201, which can be capable of resisting deformation under repeated physical stress. Examples of materials barbell-shaped enclosure 201 could be comprised of include, but are not limited to, metal, plastic, glass, composites, and/or other materials and/or or combinations of these materials. In this embodiment, barbell-shaped enclosure 201 may be the shape of a cylinder joining larger-diameter spherical shapes at either end along the long center axis, and may be of appropriate size to pierce through a lip and/or tongue of a mouth, and/or other size. In alternate embodiments, barbell-shaped enclosure 201 might have different shapes and/or sizes, including without limitation disk-shaped and/or asymmetrically-shaped ends instead of spherical ends, a larger and/or smaller size, an asymmetrical shape, a longer or shorter cylinder and/or other shapes and/or sizes. In other embodiments, barbell-shaped enclosure 201 might be shaped to grip or contact surfaces of the mouth in other ways, such as one or more oblong end shapes instead of spherical ends to allow easier rotation of the ends and/or the device, and/or one or more stylus point ends for writing and/or doing finer movements. This embodiment may be implemented using one or more components as described in FIG. 1 and/or in previous paragraphs. In this embodiment of the invention, touch sensor device 205, a pressure sensor device 250, signal light 240, and an electrical stimulator device 210 fit into the surface of barbell-shaped enclosure 201. In this embodiment of the invention, a rotation sensor device 215 bisects the cylinder, allowing for a twisting and/or rotating 216 of the ends of the device along the long center axis and compression sensor device 221, which allows the housing a compression (and/or expansion) 220 (the motion might also be used to generate power for power device 160), fits into the surface of barbell-shaped enclosure 201. In other embodiments of the invention, these devices might be differently-located, omitted, and/or duplicated at multiple locations, such as having an instance of touch sensor device 205 at both ends of the device, having rotation sensor device 215 closer to one of the ends of the cylinder section of barbell-shaped enclosure 201, or other differences.

In this embodiment of the invention, processor 110 can be a small Arduino-compatible microcontroller, and communications subsystem 130 can be a Bluetooth radio device with antenna.

In this embodiment of the invention, working memory 135 can be a flash-memory integrated circuit.

In this embodiment of the invention, multiple one or more input devices 115 can be: touch sensor device 205, a touchpad sensor; rotation sensor device 215, a rotation sensor; compression sensor device 221, a compression-sensing sensor; pressure sensor device 250, a microphone sensor; and two internal accelerometer and/or gyroscope sensor devices (one in each end of the device).

In this embodiment of the invention, power device 160 can be a battery.

In this embodiment of the invention, one or more output devices 120 are: electrical stimulator device 210, an electrical stimulator with two or more electrodes; signal light 240, an LED light; and two internal mechanical wave generator devices (one in each end of the device), vibration-producing devices.

In this embodiment of the invention, storage device 125 can be a flash-memory integrated circuit.

In this embodiment of the invention, operating system 140 can be machine code that can be read by processor 110 and can guide the functioning of device 100.

In this embodiment of the invention, application 145 can be code that can be read by processor 110 and can guide additional functioning of device 100.

Using communications subsystem 130, the embodiment of the invention illustrated in FIG. 2 might be in communication with remote devices and/or similar devices, including, but not limited to other devices in and/or on and/or near the body of the wearer (such as a head-mounted display device, a wrist-mounted display device, a pacemaker device, an insulin pump device, a mobile device, a network device, a wireless device, and/or a home automation device), and/or remote devices, and/or networks of devices, and/or devices. Merely by way of example, device 100 might allow the wearer, by interacting with one or more input devices 115, to communicate to a remote device such as a head-mounted visual display device to control a cursor or change a selection presented in the visual display device.

Figure 3:
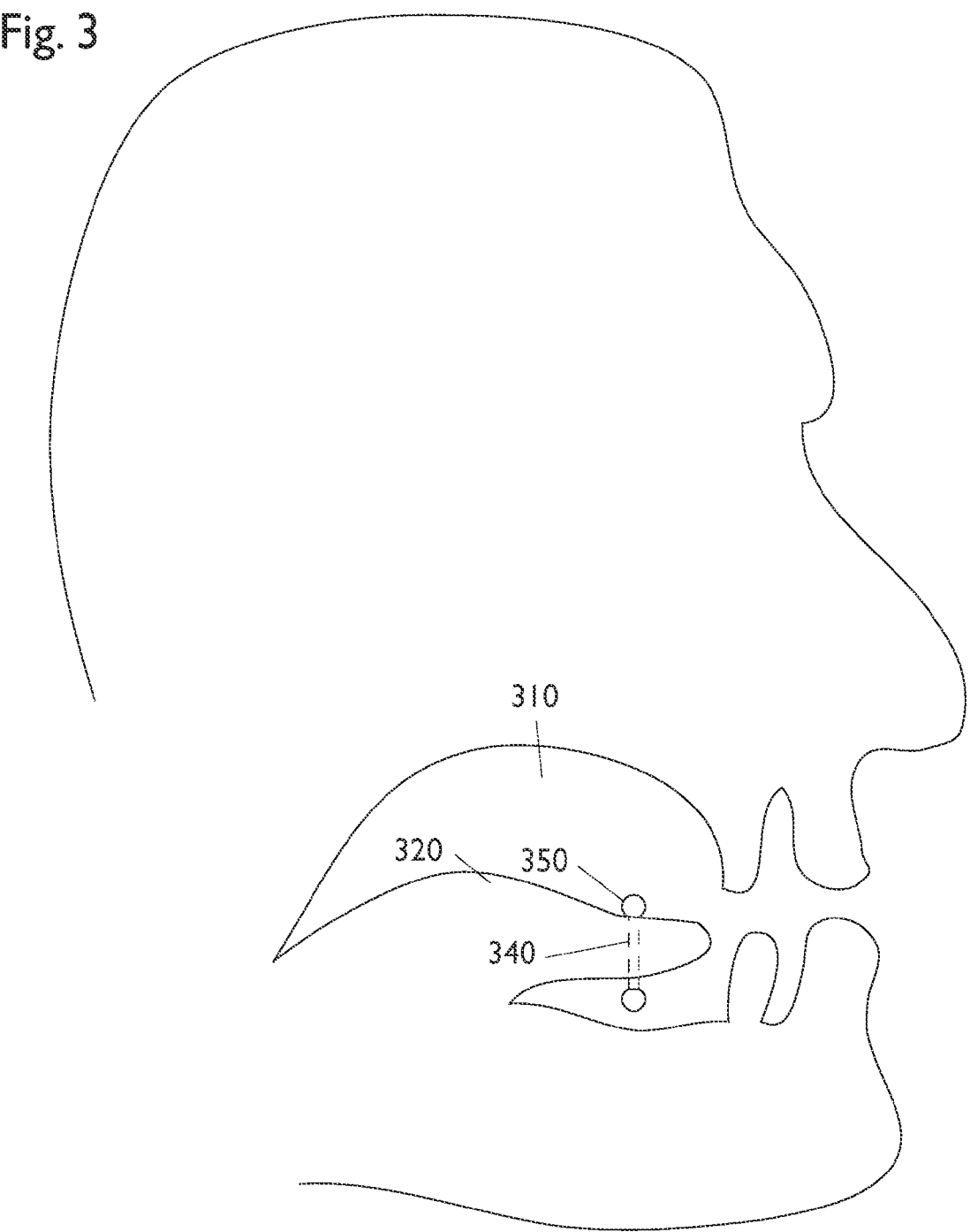
FIG. 3 is a perspective view of a cross section of a human head, showing the positioning of the device as embodied in FIG. 2.

FIG. 3 is a perspective view of a cross section of a head (in this case a human head), showing one possible position of device 350 (the device described in FIG. 2 and preceding paragraphs).

In FIG. 3, device 350 can be anchored through and/or in one or more pierced site(s) 340 around and/or in an oral cavity 310 of the wearer, through and/or in a tongue 320. In this embodiment the wearer is a human, but in other embodiments and/or usages, the wearer might be any kind of animal. In other embodiments and/or usages, positioning of device 350 might be in and/or through one or more pierced sites 340 in and/or through one or more other locations and/or one or more orientations around and/or in and/or through and/or under the tissue surrounding and/or near oral cavity 310 (such as through a lip), and/or anywhere around and/or in and/or through and/or within the body and/or form of a user. Tongue 320 (and/or other tissues of the mouth and/or body) could have one or more pierced sites 340 and/or one or more one or more devices 350 and/or other embodiments of the invention.

Oral cavity 310 and/or tongue 320 could also have multiple one or more pierced sites 340 and/or multiple one or more devices 350 and/or other devices.

Using communications subsystem 130, device 350 might be in communication with remote devices and/or similar devices, including, but not limited to other devices in and/or on and/or near the body of the wearer (such as a head-mounted display device, a wrist-mounted display device, a pacemaker device, an insulin pump device, a mobile device, a network device, a wireless device, and/or a home automation device), and/or remote devices, and/or networks of devices, and/or devices. Merely by way of example, device 350 might allow the wearer, by interacting with one or more input devices 115, to control a cursor or change a selection presented in the visual display of a separate head-mounted display device and/or provide feedback to the environment of oral cavity 310 about the remote action in the remote device in the form of a vibratory or haptic vibration within device 350.

In one embodiment, the barbell-shape of barbell-shaped enclosure 201 may be advantageous since it houses and protects the device and resists deformation under physical stress and keeps the device in pierced site 340.

In this embodiment of the invention, from pierced site 340, the input devices 115 of device 350 might observe tongue 320, the tissues of the mouth, and/or the environment of oral cavity 310 (and/or beyond): touch sensor device 205, a touchpad sensor device, can sense touch (as device 350 moves with tongue 320 and comes in contact with mouth tissues (such as the gums, teeth, lips, floor of the mouth, upper palate, and the like) and/or other objects and/or devices); rotation sensor device 215, a rotation sensor device, can sense rotation of the ends the device (this could be accomplished using the tongue or other tissues of the mouth, or by the fingers, reaching into or up to the mouth, and could, merely by way of example, be used as an on/off switch for the device); compression sensor device 221, a compression-sensing sensor device, can sense compression (and/or expansion) 220 (and compression sensor device 221 can be returned to its resting state by a spring, or the like) of the cylinder of device 350 (such as by flattening and/or fattening of tongue 320, and/or by pressing or pulling on the ends of device 350 in other ways); pressure sensor device 250, a microphone sensor device, can sense sound, such as vocalisations and/or sub-vocalisations, breathing, and other sounds that come into oral cavity 310; and two internal accelerometer and/or gyroscope sensor devices (one in each end of the device), orientation and/or acceleration sensor devices, can sense the orientation and/or acceleration of device 350 (which can be affected by actions of pierced site 340, and/or tongue 320).

In this embodiment of the invention, tongue 320, the tissues of the mouth, and/or the environment of oral cavity 310 (and/or beyond) might also observe device 350, including output devices 120 of device 350: electrical stimulator device 210 can create sensation via electric current; signal light 240 can create light and light beams; and the two internal mechanical wave generator devices (one in each end of the device), can create vibration and/or vibration differentials and/or one or more stereo vibration fields and/or haptic fields and/or patterns.

In this embodiment of the invention, the dexterity, and/or communication abilities of the mouth can now be used for, among other things, fine control, interaction, and exchange of information to and/or from and/or through device 350.

Using one or more input devices 115, some embodiments of the invention might observe and act on analog input from the environment of the mouth and/or entering the environment of the mouth, such as a material sensor device being used to monitor and/or analyze and/or report blood chemical levels, gas levels in the breath, and/or chemical makeup of food ingested of and/or by the user.

Figure 4:
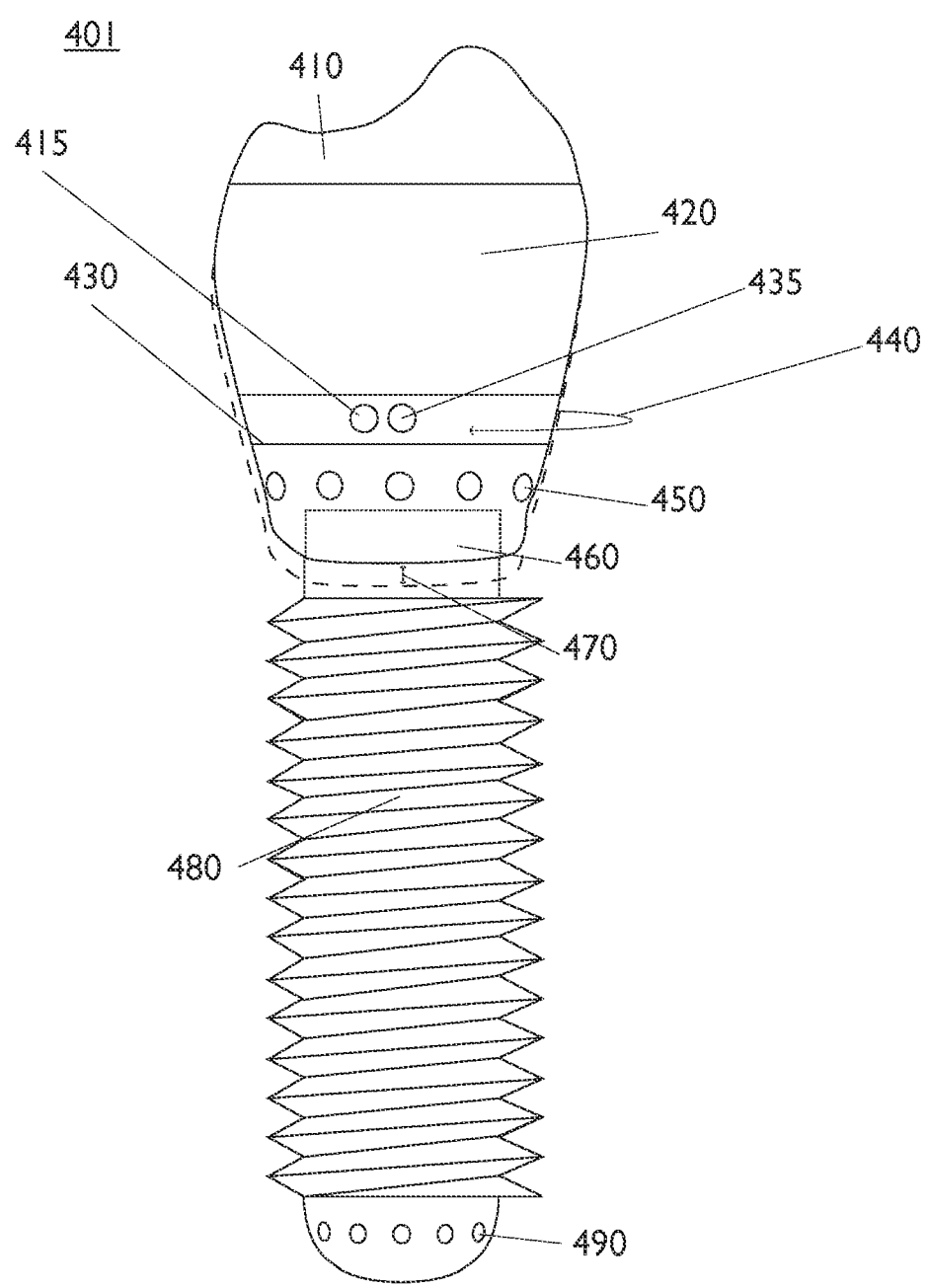
FIG. 4 is a perspective view of a tooth-implant embodiment of the device.

FIG. 4 is a perspective view of a tooth-implant shaped enclosure, according to another embodiment of the present invention. Tooth implant shaped enclosure 401 may be implemented using one or more components as described in FIG. 1 and/or in previous paragraphs.

In this embodiment, tooth implant shaped enclosure 401 has a tooth-shaped enclosure 410 of ceramic or other material that houses and protects the device. Tooth-shaped enclosure 410 looks similar to a tooth or teeth. In other embodiments, tooth-shaped enclosure 410 might mimic, partially mimic, and/or not mimic other structures, and/or have a different shape and/or shapes.

Tooth-shaped enclosure 410 may house touch sensor device 420 (a touch-sensing device, such as a touchpad, which can wrap around tooth shaped enclosure 410), rotation sensor device 430 (that can sense twisting or rotating 440), compression sensor device 460 (that can sense compression (and expansion) 470), electrical stimulator device 450, and may have tooth implant anchor 480, which may also have anchor electrical stimulator device 490. In other embodiments, tooth implant shaped enclosure 401 might lack tooth implant anchor 480, and, instead connect to an external tooth implant via an implant connection socket.

Figure 5:
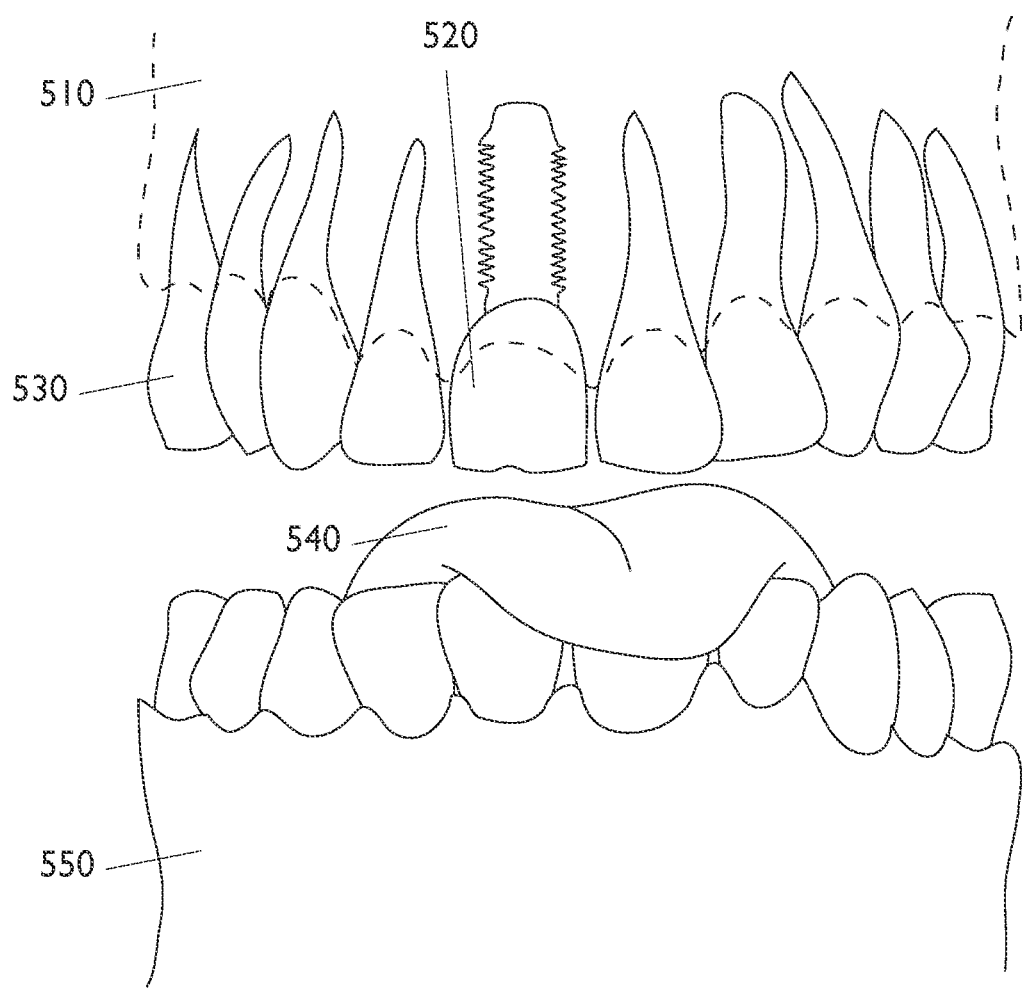
FIG. 5 is a perspective view of the teeth, gums and tongue of a human mouth, showing the position of the device as embodied in FIG. 4.

FIG. 5 is a perspective view inside a mouth, with teeth (including tooth 530), upper gums/maxilla 510, lower gums/mandible 550 and tongue 540, with upper gums/maxilla 510 hidden to show the full teeth. FIG. 5 shows the device, as embodied in FIG. 4, worn in one possible tooth implant location 520 in the upper gums/maxilla 510. This embodiment may be implemented using one or more components as described in FIG. 1 and/or in previous paragraphs.

In this embodiment of the device, one or more input devices 115 may include without limitation: one or more touch sensor devices 420 (built into the surface of the housing) that responds to touch input and/or can create 'mouse'-type positioning, tap, pressure, coverage and/or touch-related data; compression sensor device 460 inside the housing that responds to compression (and expansion) 470 along the length of the housing; a rotation sensor device 430 in the housing that can sense twisting or rotating 440 the two ends of the device; a pressure sensor device 435 that responds to air pressure; and one or more internal accelerometer and/or gyroscope sensor devices, orientation and/or acceleration sensor devices that can sense the orientation and/or acceleration of tooth implant shaped enclosure 401.

In this embodiment of the device, one or more output devices 120 may include without limitation: a mechanical wave generator device that can be a vibration device and/or or a speaker device (a vibration device creates vibration in the device using a vibration motor device or other vibration-causing device, a speaker device creates sound waves from the device by creating movement using a speaker or other movement-creating device); signal light 415, a light device (a light device can display one or more lights and/or beams of light) that displays a light; an electrical stimulator device 450 that can create sensation in the wearer via electric shocks from electrodes, and/or anchor electrical stimulator device 490, that can create sensation in the wearer via electric shocks from electrodes. The actions of the output devices 120 can be perceived by the user and/or others.

FIG. 5 is a perspective view of the teeth, gums and tongue of a human mouth, showing the position of the device as embodied in FIG. 4. This embodiment may be implemented using one or more components as described in FIG. 1 and/or in previous paragraphs. In this embodiment of the invention, the device can be worn in a user's mouth, such as in FIG. 5, embedded in upper gums/maxilla 501, or lower gums/mandible 550 by the titanium (or other, suitable material) threads of tooth implant anchor 480. In this placement of the device, one or more input devices 115 (such as touch sensor device 420, compression sensor device 460, rotation sensor device 430, pressure sensor device 435, and the internal accelerometer and/or gyroscope sensor device) can be manipulated by the tongue 540, lips, other parts of the mouth and/or by other means (such as movement of the head or jaw).

Figure 6:
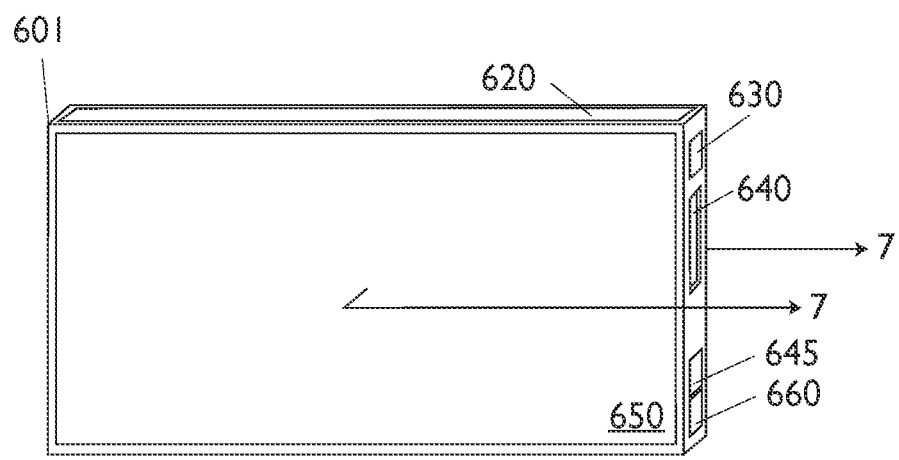
FIG. 6 is a perspective view of a dental bridge embodiment of the device.

FIG. 6 is a perspective view of a dental bridge-shaped enclosure, according to an embodiment of the present invention. This embodiment may be implemented using one or more components as described in FIG. 1 and/or in previous paragraphs. The dental bridge-shaped enclosure includes without limitation bridge enclosure 601 of metal, pyrex, plastic, or other material or materials that houses and protects the device. Bridge enclosure 601 can be affixed to the teeth of the mandible via regular bridge attachment methods or as part of a dental retainer, such as a Hawley retainer.

Bridge enclosure 601 can allow one or more input devices 115 to observe the environment around the device and one or more output devices 120 to act (directly or indirectly) on the environment around bridge enclosure 601, while sealing and protecting device 100 from damage.

In this embodiment of the invention, one or more input devices 115 may include: a touch sensor device 650 (built into the surface of the housing) that can respond to touch input and/or can create 'mouse'-type positioning, tap, pressure, coverage and/or touch-related data; a compression sensor device 620 inside the housing; a compression switch 630; a pressure sensor device 660 that can respond to air pressure, and a internal accelerometer and/or gyroscope sensor device, orientation and/or acceleration sensor devices that can sense the orientation and/or acceleration of bridge enclosure 601.

In this embodiment of the invention, one or more output devices 120 may include, but are not limited to: a mechanical wave generator device that can create vibrations from a vibration motor device; a light device that can display a signal light 640; and a shock device that creates small electric shocks from an electrodes of electrical stimulator device 645, arrayed on the surface of the device.

Figure 7:
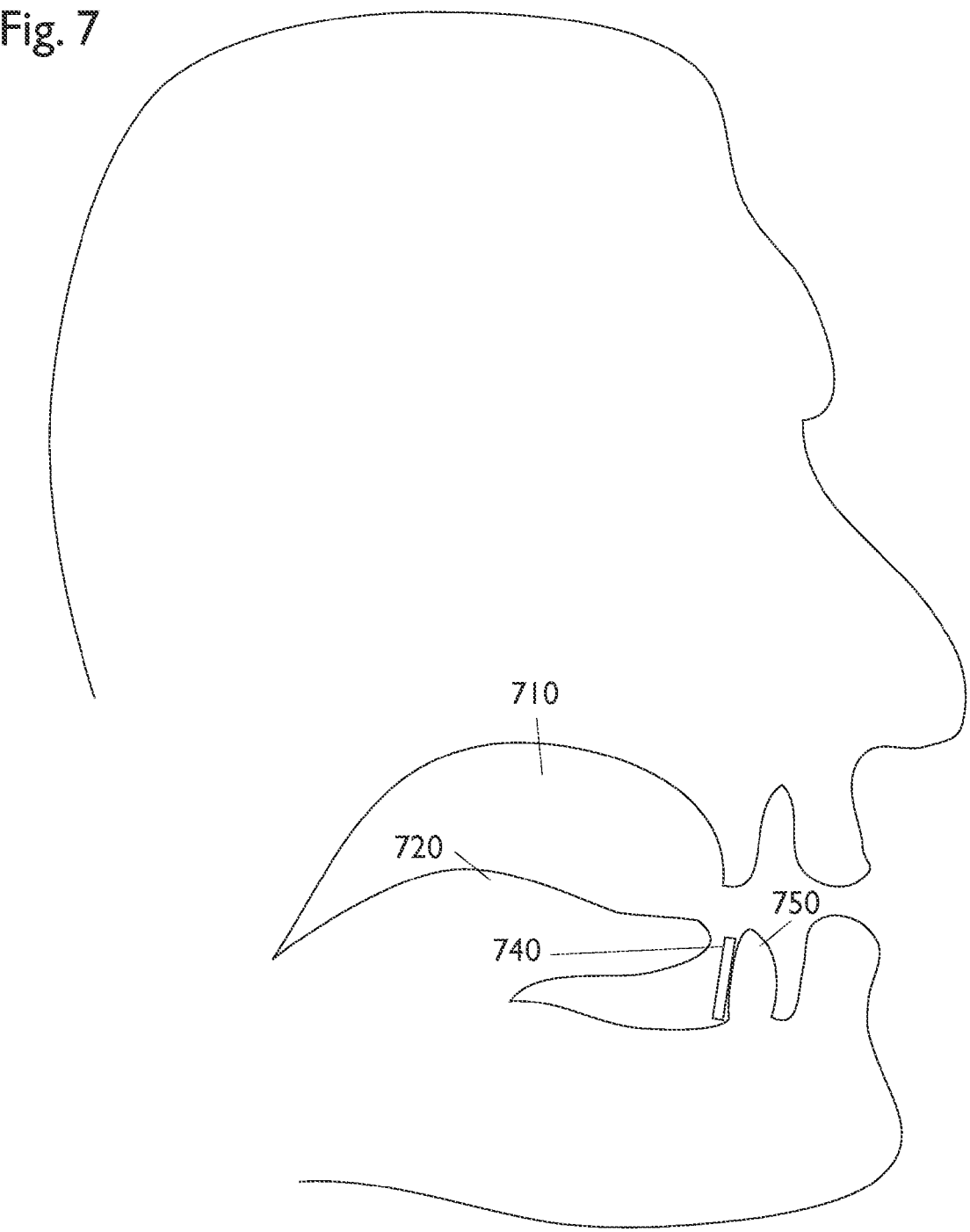
FIG. 7 is a perspective view of a cross section of a human head, showing the positioning of the device as embodied in FIG. 6.

FIG. 7 is a perspective view of a cross section of a human head, cut away to show the oral cavity 710, the tongue 720, and the device 740, as embodied in FIG. 6, worn in one possible location, affixed to the teeth of mandible 750 in the orientation as indicated by lines 7-7 in FIG. 6. This embodiment may be implemented using one or more components as described in FIG. 1 and/or in previous paragraphs.

In this embodiment, the device can be worn in a user's mouth, such as in FIG. 7, affixed to the teeth of the mandible 750. In this placement of the device, tongue 720 can access touch sensor device 650, and compression sensor device 620 can be manipulated by the tongue 720, lips, other parts of the mouth and/or by other means. And the actions of one or more output devices 120 can be perceived by the user and/or others. In regular operation of the device, tongue 720 can stay in a fairly relaxed position along the mandible and can stay clear of blocking most regular mouth function.

FIG. 8 is a flow diagram of the general method for communicating 801 used by the some embodiments of the invention, comprised of three steps: step one—generating stimulus to a tongue of a user to communicate a user interface to the user 810; step two—detecting analog input from an environment of the tongue of the user 820; and step three—interpreting the analog input from the environment as one or more user commands 830.

In step one, generating a stimulus to a tongue of a user to communicate a user interface to the user 810, some of the user interface, the system by which the user interacts with the device, is communicated to the user via one or more output devices 120. For example, without limitation, one or more points of stimulus (perhaps each with a distinct pattern or signature of stimulation) might be generated by electrical stimulator device 210 to the tongue of the user, representing information and/or distinct options and/or choices of operating system 140 and/or one or more applications 145 to be perceived by the user. In other embodiments, without limitation, the stimulus of step one might involve one or more various patterns, sequences, loops, haptic signatures, intensities, orientations, locations, apparent locations, stereo locations, verbosities, speeds, scales, tones, and the like and/or can be used to communicate information to the user, including, but not limited to, information about the state of one or more processors 110, working memory 135, operating system 140, one or more applications 145, external devices, and the like.

In step two, detecting analog input from an environment of the tongue of the user 820, analog input, states and/or activity in the mouth environment can be received and/or detected by one or more input devices 115 and/or can be stored in working memory 135 and/or storage device 125 and/or device 100.

In step three, interpreting the analog input from the environment as one or more user commands 830, the analog input detected and/or stored in step two can be interpreted by one or more processors 110 and/or operating system and/or one or more applications 145 as one or more user commands, instructions that can be converted by device 100 to the appropriate operating system 140 function and/or functions. For example, without limitation, fattening and/or flattening of the user's tongue, detected by compression sensor device 221, might be interpreted as a user command to select, and/or cycle through choices or options of operating system 140, and/or one or more applications 145.

In some embodiments of the invention, the wearer of the device can use the device to communicate to one or more external devices, including, but not limited to, communicating commands and data with other devices, and communicating input and/or about input detected by one or more input devices 115. Merely by way of example, device 100 could be used to analyze accelerometer and/or gyroscopic and/or audio data about vocalizations (or sub-vocalizations) and tongue position to compare or predict text of speech.

Figure 9:
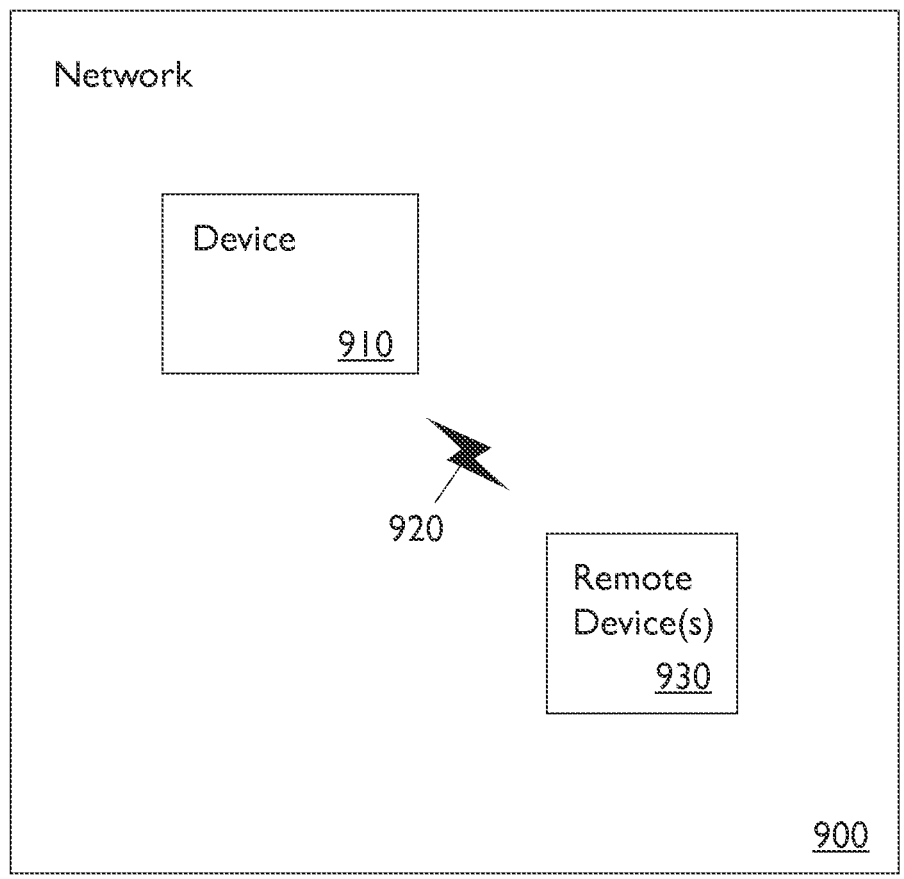
FIG. 9 illustrates an exemplary network of devices.

FIG. 9 illustrates a schematic drawing of an example computer network infrastructure. Device 910 may be implemented using one or more components as described in FIG. 1, and/or other figures, and/or in previous paragraphs. In network 900, device 910 communicates using a communication link 920 (e.g., a wired or wireless connection, implemented by communications subsystem 130) with one or more external or remote devices 930 (which can be, without limitation, in various proximity to device 910, for example in the same mouth, or across a distance of miles to a communications tower). Communication link 920 may be one way (in either direction) or two way (for example, device 910 could receive a transmission from, transmit to, or receive from and transmit to one or more remote devices 930). Remote device 930 may be any type of device that can receive and/or transmit data. Device 910 can act as a hub or spoke of the network. Remote device 930 might act as a hub or spoke of the network. One more more remote devices 930 might have communication 920 with device 910, and/or other communication between remote devices 930. Network communication is therefore possible. Merely by way of example, device 100 could be used to send data detected by touch sensor device 650 as mouse-type data to one or more remote devices 930, such a laptop computer, in order to control its mouse and/or cursor. Merely by way of example, device 100 could be used to receive and compare data detected by pressure sensor device 250 with data communicated 920 from one or more remote devices 930, such a laptop computer with a microphone and a wireless card, in order to compare and/or clarify vocalized sounds.

The methods, systems, and devices discussed above are examples. Various embodiments may omit, substitute, or add various procedures or components as appropriate. For instance, in alternative configurations, the methods described may be performed in an order different from that described, and/or various stages may be added, omitted, and/or combined. Also, features described with respect to certain embodiments may be combined in various other embodiments. Different aspects and elements of the embodiments may be combined in a similar manner. Also, technology evolves and, thus, many of the elements are examples that do not limit the scope of the disclosure to those specific examples.

Specific details are given in the description to provide a thorough understanding of the embodiments. However, embodiments may be practiced without these specific details. For example, well-known circuits, processes, algorithms, structures, and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention.

Also, some embodiments were described as processes depicted as flow diagrams or block diagrams. Although each may describe the operations as a sequential process, many of the operations can be performed in parallel or concurrently. In addition, the order of the operations may be rearranged. A process may have additional steps not included in the figure. Furthermore, embodiments of the methods may be implemented by hardware, software, firmware, middleware, microcode, hardware description languages, or any combination thereof. When implemented in software, firmware, middleware, or microcode, the program code or code segments to perform the associated tasks may be stored in a computer-readable medium such as a storage medium. Processors may perform the associated tasks.

Having described several embodiments, various modifications, alternative constructions, and equivalents may be used without departing from the spirit of the disclosure. For example, the above elements may merely be a component of a larger system, wherein other rules may take precedence over or otherwise modify the application of the invention. Also, a number of steps may be undertaken before, during, or after the above elements are considered. Accordingly, the above description does not limit the scope of the disclosure.

What is claimed is:

1. An apparatus comprising:
    a housing anchored in a mouth of an animal and resistant to damage from bodily fluids and pressure, wherein the housing is a tongue, lip, or cheek piercing and further comprises:
        an input device sensing an input from a user;
        a processor communicatively coupled with the input device and configured to process input from the input device;
        an output device communicatively coupled to the processor, wherein the output device communicates a user interface to the user by applying a stimulus to the mouth;
        a memory storage device communicatively coupled to the processor, wherein the memory storage device stores and recalls data;
        a communication subsystem coupled to the processor, wherein the communication subsystem communicates with a remote device placed outside the mouth; and
        a power device powering the input device, the processor, the output device, the memory storage device, or the communication subsystem.

2. The apparatus of claim 1, wherein the housing is a barbell-shape.

3. The apparatus of claim 1, wherein the input device comprises an analog sensor, a touchpad, a microphone, a pushbutton, a gyroscope, an accelerometer, a movement tracking sensor, a light emitting diode (LED) tracking device, a photo-diode tracking device, a pressure sensor, a piezoelectric device, an air pressure sensor, an input switch, a slider, a bite pressure sensor, an optical touch device, a rotation sensor, a light sensor, on/off switch, or orientation sensor.

4. The apparatus of claim 1, wherein the input device comprises a temperature sensor, an olfaction sensor, a gas flow monitor, a chemical identification device, or a material sensor.

5. The apparatus of claim 1, wherein the input device comprises a compression sensor, wherein the compression sensor, by detecting compression or expansion of a portion of the housing, senses flattening of the tongue, fattening of the tongue, pressing an end of the housing, or pulling the end of the housing.

6. The apparatus of claim 1, wherein the output device comprises an electrical stimulator, a light emitter, a vibrator, a physical matter release device, or a mechanical wave generator.

7. The apparatus of claim 1, wherein the user interface, by way of the stimulus, presents options, choices, information about a state of the processor, information about a state of the storage device, information about an operating system, information about an application, or information about the remote device.

8. The apparatus of claim 1, wherein the stimulus represents the user interface by way of a pattern of stimulation, a signature of stimulation, a sequence of stimulation, a loop of stimulation, intensity of stimulation, orientation of stimulation, location of stimulation, apparent location of stimulation, stereo location of stimulation, verbosity of stimulation, speed of stimulation, scale of stimulation, or tone of stimulation.

9. The apparatus of claim 1, wherein the communication subsystem comprises a wired network communications device, a wireless network communications device, an infrared communication device, an optical communications device, a wireless communication device, a wireless communication chipset, a Bluetooth® device, a radio frequency identification (RFID) device, an active RFID device, a passive RFID device, a battery-assisted RFID device, an 802.11 device, a Wi-Fi® device, a WiMAX® device, a cellular communication facility, or an electromagnetic field (EMF) transmitter/receiver device.

10. The apparatus of claim 1, further comprising the remote device, wherein the remote device comprises a wheelchair, a computer, a text-to-speech device, a head-mounted display, a wrist-mounted display, a pacemaker, an insulin pump, a mobile device, a network device, a wireless device, or a home automation device.

11. The apparatus of claim 1, wherein the power device comprises a battery, a power generator, a power management device, a connection to a second power device residing external to the housing, a power transfer device transferring power from the second power device, a power generator generating power by way of interaction with chemicals internal to the housing, a power generator generating power by way of interaction with chemicals external to the housing, a power generator generating power by way of interaction with chemicals in a bloodstream of the user, a power generator generating power by way of interaction with pressure in the bloodstream, a power generator generating power by way of functioning of organisms, a genetically-engineered biofuel device, a biofuel organism that generates power from oxygen and glucose in the bloodstream, a power generator generating power by way of temperature differences, a power generator generating power by way of movement, a power generator generating power by way of wireless energy transfer, a power generator generating power by way of compression of the housing, or a power generator generating power by way of expansion of the housing.

12. A method comprising:
anchoring a housing in a mouth of an animal, wherein the housing is resistant to damage from bodily fluids and pressure and is a tongue, lip, or cheek piercing;
sensing, by an input device of the housing, an input from a user;
processing, by a processor of the housing and communicatively coupled with the input device, input from the input device;
communicating, by an output device of the housing and communicatively coupled to the processor, a user interface to the user by applying a stimulus to the mouth;
storing and recalling, by a memory storage device of the housing and communicatively coupled to the processor, data;
communicating, by a communication subsystem of the housing and communicatively coupled to the processor, with a remote device placed outside the mouth; and
powering, by a power device of the housing, the input device, the processor, the output device, the memory storage device, or the communication subsystem.

13. The method of claim 12, wherein the housing is a barbell-shape.

14. The method of claim 12, wherein the input device comprises an analog sensor, a touchpad, a microphone, a pushbutton, a gyroscope, an accelerometer, a movement tracking sensor, a light emitting diode (LED) tracking device, a photo-diode tracking device, a pressure sensor, a piezoelectric device, an air pressure sensor, an input switch, a slider, a bite pressure sensor, an optical touch device, a rotation sensor, a light sensor, on/off switch, or orientation sensor.

15. The method of claim 12, wherein the input device comprises a temperature sensor, an olfaction sensor, a gas flow monitor, a chemical identification device, or a material sensor.

16. The method of claim 12, wherein the input device comprises a compression sensor, wherein the compression sensor, by detecting compression or expansion of a portion of the housing, senses flattening of the tongue, fattening of the tongue, pressing an end of the housing, or pulling the end of the housing.

17. The method of claim 12, wherein the output device comprises an electrical stimulator, a light emitter, a vibrator, a physical matter release device, or a mechanical wave generator.

18. The method of claim 12, wherein the user interface, by way of the stimulus, presents options, choices, information about a state of the processor, information about a state of the storage device, information about an operating system, information about an application, or information about the remote device.

19. The method of claim 12, wherein the stimulus represents the user interface by way of a pattern of stimulation, a signature of stimulation, a sequence of stimulation, a loop of stimulation, intensity of stimulation, orientation of stimulation, location of stimulation, apparent location of stimulation, stereo location of stimulation, verbosity of stimulation, speed of stimulation, scale of stimulation, or tone of stimulation.

20. The method of claim 12, wherein the communication subsystem comprises a wired network communications device, a wireless network communications device, an infrared communication device, an optical communications device, a wireless communication device, a wireless communication chipset, a Bluetooth® device, a radio frequency identification (RFID) device, an active RFID device, a passive RFID device, a battery-assisted RFID device, an 802.11 device, a Wi-Fi® device, a WiMAX® device, a cellular communication facility, or an electromagnetic field (EMF) transmitter/receiver device.

21. The method of claim 12, further comprising the remote device, wherein the remote device comprises a wheelchair, a computer, a text-to-speech device, a head-mounted display, a wrist-mounted display, a pacemaker, an insulin pump, a mobile device, a network device, a wireless device, or a home automation device.

22. The method of claim 12, wherein the power device comprises a battery, a power generator, a power management device, a connection to a second power device residing external to the housing, a power transfer device transferring power from the second power device, a power generator generating power by way of interaction with chemicals internal to the housing, a power generator generating power by way of interaction with chemicals external to the housing, a power generator generating power by way of interaction with chemicals in a bloodstream of the user, a power generator generating power by way of interaction with pressure in the bloodstream, a power generator generating power by way of functioning of organisms, a genetically-engineered biofuel device, a biofuel organism that generates power from oxygen and glucose in the bloodstream, a power generator generating power by way of temperature differences, a power generator generating power by way of movement, a power generator generating power by way of wireless energy transfer, a power generator generating power by way of compression of the housing, or a power generator generating power by way of expansion of the housing.

\* \* \* \* \*